(12) United States Patent
Visser (10) Patent No.: US 10,175,218 B2
(45) Date of Patent: Jan. 8, 2019

(54) CLASSIFICATION OF SOIL TEXTURE AND CONTENT BY NEAR-INFRARED SPECTROSCOPY

(71) Applicant: Farmers Edge Inc., Winnipeg (CA)

(72) Inventor: Patrick J. Visser, Winnipeg (CA)

(73) Assignee: FARMERS EDGE INC., Winnipeg, Manitoba (CA)

( * ) Notice: Subject to any disclaimer, the term of this patent is extended or adjusted under 35 U.S.C. 154(b) by 0 days.

(21) Appl. No.: 15/840,575

(22) Filed: Dec. 13, 2017

(65) Prior Publication Data

US 2018/0172659 A1 Jun. 21, 2018

Related U.S. Application Data

(60) Provisional application No. 62/435,655, filed on Dec. 16, 2016.

(51) Int. Cl.
*G01N 33/24* (2006.01)
*G01N 21/359* (2014.01)

(52) U.S. Cl.
CPC ........... *G01N 33/24* (2013.01); *G01N 21/359* (2013.01)

(58) Field of Classification Search
CPC .............................. G01N 21/359; G01N 33/24
See application file for complete search history.

(56) References Cited

U.S. PATENT DOCUMENTS

| | | | |
|---|---|---|---|
| 6,608,672 B1 | 8/2003 | Shibusawa et al. | |
| 6,937,939 B1 * | 8/2005 | Shibusawa | G01N 21/314 |
| | | | 250/255 |
| 9,285,501 B2 | 3/2016 | Christy et al. | |
| 9,309,157 B2 | 4/2016 | Fujisaki et al. | |
| 9,329,122 B2 | 5/2016 | Herron et al. | |
| 9,360,421 B2 | 6/2016 | Lanan et al. | |

(Continued)

FOREIGN PATENT DOCUMENTS

| | | |
|---|---|---|
| CA | 2089096 A1 | 6/1992 |
| CA | 2069392 C | 12/1995 |

(Continued)

OTHER PUBLICATIONS

PCT International Search Report and Written Opinion, PCT Application No. PCT/CA2017/051508, dated Apr. 5, 2018, 7 pages.

(Continued)

*Primary Examiner* — Mark R Gaworecki
(74) *Attorney, Agent, or Firm* — Fenwick & West LLP (57) ABSTRACT

This description relates to a predictive model for estimating the proportions of sand, silt, and clay in a soil sample based on near-infrared spectroscopy (NIRS) performed on the soil samples. The soil texture prediction model is trained using benchmark NIRS test data and collected spectra of soil samples for which the benchmark test data has been collected. The estimates produced by the model can be used to determinate a variety of properties of the soil sample, such as hydrological properties and soil quality. Knowledge of these properties are useful for informing decisions that agronomists, producers, or farm managers make throughout the year. For example, agronomists use the determined properties to infer how the soil will perform under any given treatment or application, for example applying seeds, fertilizer, pesticide, and herbicide.

20 Claims, 11 Drawing Sheets

(56) References Cited

U.S. PATENT DOCUMENTS

2015/0310633 A1   10/2015  Nelan
2017/0090068 A1    3/2017  Xiang et al.
2017/0122889 A1    5/2017  Weindorf et al.

FOREIGN PATENT DOCUMENTS

| | | |
|---|---|---|
| CA | 2220913 A1 | 5/1999 |
| CA | 2025329 C | 8/2001 |
| CA | 2432605 A1 | 7/2002 |
| CA | 2801379 A1 | 12/2011 |
| CN | 101975764 A | 2/2011 |
| EP | 1203955 A1 | 5/2002 |
| EP | 1203955 A4 | 7/2003 |
| EP | 1143784 B1 | 2/2007 |
| WO | WO 2000/054566 A2 | 9/2000 |
| WO | WO 2000/054566 A3 | 9/2000 |
| WO | WO 2004/079365 A1 | 9/2004 |
| WO | WO 2010/129877 A1 | 11/2010 |
| WO | WO 2015/195988 A1 | 12/2015 |
| WO | WO 2016/077421 A1 | 5/2016 |
| WO | WO 2016/186507 A1 | 11/2016 |
| WO | WO 2016/201508 A1 | 12/2016 |
| WO | WO 2017/053273 A1 | 3/2017 |

OTHER PUBLICATIONS

Mouazen et al., "Classification of Soil Texture Classes by Using Soil Visual Near Infrared Spectroscopy and Factorial Discriminant Analysis Techniques," Near Infrared Spectrosc., 2005, pp. 231-240, vol. 13, No. 4.

Saxton, et al., "Soil Water Characteristics Estimates by Texture and Organic Matter for Hydrologic Solutions," Soil Sci. Soc. Am., 2006, pp. 1569-1578, vol. 70.

* cited by examiner

F:\NIR Calibration Work\2016-08-31 – Q2 – Clay and Sand – Cleaned Cal Data\Clay Q2
Clay 2016-09-12.q2
Validation No 9 +

Clay                                                    Rank: 17

Validation Report

General Information

| | |
|---|---|
| Method File: | Clay 2016-09-12.q2 |
| Standards (total): | 925 |
| Calibration Spectra: | 897 |
| Test Spectra: | 0 |
| Data Block: | AB |
| Components (total): | 1 |
| Frequency Regions: | 2 |
| Selected Datapoints: | 332 |
| Mean Centering: | Yes |
| Preprocessing: | First derivative |
| Smoothing Points: | 17 |

Frequency Regions

| from | to | | | |
|---|---|---|---|---|
| 7405.8 | 6703.8 | | | |
| 5492.6 | 3648.9 | | | |

Clay

| | |
|---|---|
| Component Range: | 4.046 – 83.07 |
| Component Unit: | % |
| Validation Type: | Cross Validation |
| No. of samples leaving out: | 18 |

*FIG. 5*

F:\NIR Calibration Work\2016-08-31 -- Q2 -- Clay and Sand -- Cleaned Cal Data\Clay Q2
Clay 2016-09-12.q2
Validation No 9 +

Clay                                          Rank: 17

Mean Prediction Error

| Rank | R² | RMSECV | Rec. Rank |
|---|---|---|---|
| 1 | 25.3 | 13.2 | |
| 2 | 35.24 | 12.3 | |
| 3 | 44.42 | 11.4 | |
| 4 | 56.33 | 10.1 | |
| 5 | 67.24 | 8.75 | |
| 6 | 75.77 | 7.52 | |
| 7 | 78.27 | 7.13 | |
| 8 | 81.06 | 6.65 | |
| 9 | 84.99 | 5.92 | |
| 10 | 86.78 | 5.56 | |
| 11 | 87.8 | 5.34 | |
| 12 | 88.36 | 5.22 | |
| 13 | 88.93 | 5.08 | |
| 14 | 89.13 | 5.04 | |
| 15 | 89.54 | 4.94 | |
| 16 | 89.71 | 4.9 | |
| 17 | 89.86 | 4.87 | + |
| 18 | 89.95 | 4.85 | |
| 19 | 90.16 | 4.79 | |
| 20 | 90.04 | 4.82 | |
| 21 | 90.1 | 4.81 | |
| 22 | 90.11 | 4.81 | |
| 23 | 90.17 | 4.79 | |
| 24 | 89.97 | 4.84 | |
| 25 | 90.06 | 4.82 | |
| 26 | 90 | 4.83 | |
| 27 | 90.03 | 4.83 | |
| 28 | 90.21 | 4.78 | |
| 29 | 90.16 | 4.79 | |
| 30 | 90.13 | 4.8 | |

*FIG. 6*

Clay                                   Rank: 17

| | File Name | True | Prediction | Difference | Possible Outl. |
|---|---|---|---|---|---|
| | Component Values | | | | |
| | Used Rank: | 17 | | | |
| 2 | 131202_020-0 | 32.0323 | 33.8 | -1.77 | |
| 3 | 131202_023-0 | 28.09 | 23.35 | 4.74 | |
| 4 | 131202_029-0 | 26.0483 | 22.75 | 3.29 | |
| 5 | 131202_044-0 | 36.0323 | 42.56 | -6.53 | |
| 6 | 131202_054-0 | 32.0451 | 30.8 | 1.24 | |
| 7 | 131202_056-0 | 12.0648 | 19.22 | -7.16 | |
| 8 | 131202_056-0 | 21.9856 | 19.17 | 2.81 | |
| 9 | 131202_056-0 | 32.0464 | 27.18 | 4.86 | |
| 10 | 131202_057-0 | 26.0692 | 29.54 | -3.47 | |
| 11 | 131202_059-1 | 26.0639 | 22.98 | 3.09 | |
| 12 | 131202_061-0 | 30 | 29.55 | 0.446 | |
| 13 | 131202_062-0 | 30.0419 | 22.86 | 7.18 | |
| 14 | 131202_063-0 | 29.0068 | 26.43 | 2.58 | |
| 15 | 131202_075-0 | 34.09 | 37.6 | -3.51 | |
| 16 | 131202_114-0 | 35.0529 | 22.94 | 12.1 | |
| 17 | 131202_138-0 | 29.9461 | 31.97 | -2.02 | |
| 18 | 131202_160-0 | 26.102 | 27.84 | -1.74 | |
| 19 | 131202_166-0 | 48.0156 | 40.11 | 7.9 | |
| 20 | 131203_007-0 | 38.0715 | 35.72 | 2.35 | |
| 21 | 131203_007-0 | 39.0629 | 39.24 | -0.178 | |
| 22 | 131203_009-0 | 36.0587 | 34.31 | 1.75 | |
| 23 | 131203_009-0 | 37.102 | 33.89 | 3.21 | |
| 24 | 131203_009-1 | 37.0723 | 37.45 | -0.379 | |
| 25 | 131203_028-0 | 26.0759 | 23.96 | 2.11 | |
| 27 | 131203_051-0 | 37.102 | 29.97 | 7.13 | |
| 28 | 131203_058-0 | 37.992 | 30.83 | 7.17 | |
| 29 | 131203_059-0 | 37.9996 | 38.46 | -0.465 | |
| 30 | 131203_060-0 | 33.9992 | 34 | 0.00377 | |
| 31 | 131203_067-0 | 38.004 | 36.52 | 1.48 | |
| 32 | 131203_067-0 | 37.0152 | 31.34 | 5.67 | |
| 33 | 131203_067-0 | 38.0335 | 35.51 | 2.52 | |
| 34 | 131203_068-0 | 42.0683 | 40.72 | 1.35 | |
| 36 | 131203_152-1 | 31.0771 | 22.19 | 8.89 | |
| 37 | 131203_177-0 | 69.0976 | 70.44 | -1.34 | |
| 38 | 131203_177-0 | 66.1426 | 66.55 | -0.402 | |
| 39 | 131203_178-0 | 68.222 | 75.26 | -7.04 | |

*FIG. 7*

| "C:\temp\2017\11\171101_001-02_6-24.0" 1 | Spectral Residuals | Values |
|---|---|---|
| Quant Report AB | F Prob Limit: | 0.99 |
| ⊟ PLS Analysis Report | | |
| ⋮ Spectral Residuals | | |
| ⊟ PLS Analysis Report | | |
| ⋮ Spectral Residuals | | |

| Component | Mean Residual | Residual | F Value | F Prob | Outlier |
|---|---|---|---|---|---|
| Clay | 6.78E-005 | 5.65E-005 | 0.695 | 0.595 | |

*FIG. 8*

| "C:\temp\2017\11\171101_001-02_6-24.0" 1 | Spectral Residuals | Values | | | |
|---|---|---|---|---|---|
| Quant Report AB | F Prob Limit: | 0.99 | | | |
| ⊟ PLS Analysis Report | Component | Mean Residual | Residual | F Value | F Prob | Outlier |
| ⋯ Spectral Residuals | | | | | |
| ⊟ PLS Analysis Report | Sand | 4.27E-005 | 4.31E-005 | 1.02 | 0.687 | |
| ⋯ Spectral Residuals | | | | | | |

Result of QUANT evaluation:

Spectrum file: C:\temp\2017\11\171101_001-02_24.0
Date and time (measurement): 08/11/2017 13:34:40.242 (GMT-6)

| Component | Prediction | Unit |
|---|---|---|
| Clay | 41.02 | % |
| Sand | 17.48 | % |

CLASSIFICATION OF SOIL TEXTURE AND CONTENT BY NEAR-INFRARED SPECTROSCOPY

RELATED APPLICATION INFORMATION

This application claims priority to U.S. Provisional Patent Application 62/435,655 filed on Dec. 16, 2016.

TECHNICAL FIELD

The present disclosure generally relates to a method for soil sampling for agriculture, more specifically for classification of soil characteristics.

BACKGROUND

There are a number of existing methods for measuring the soil hydrologic properties such as field capacity (FC), saturation (Sat), permanent wilting point (PWP), and plant available water (PAW). One method is to directly measure these quantities in the physical laboratory using a tension table. Meanwhile, other methods estimate these hydrologic properties, such as pedotransfer functions (PTFs), compaction, electrical conductivity, salinity, gravel content etc., which evaluate several soil properties including: sand, clay, and soil organic matter (SOM), among others; which derive these output quantities using associated mathematical functions. PTFs, also referred to as PTF models, vary by regional design and may include other model inputs with varying degrees of sensitivity.

When hydrologic properties are estimated using PTFs the model inputs are typically acquired through laboratory analysis via pipette, using sedimentation methods, or inferred from infield mapping of soil electrical conductivity. These processes are costly with respect to human labor and laboratory footprint. As a result, PTFs are not used in commercial agronomic practice due to the high cost of analysis. Particularly, using an infield instrument that can spatially map electrical conductivity involves pulling along an electromagnetic instrument over the field and collecting the electrical conductivity of the soil underneath the instrument; this method is expensive, and does not scale well to a large service offering covering a large number of acres.

SUMMARY

This disclosure relates to a nutrient planning system and method allows novice or intermediate agronomists, producers, or farm managers to create high quality crop-nutrition plans that enable sustainable, efficient, and traceable food production. The system and method particularly provides an output that can feed into an agronomic model.

One of the outputs of the system and method is an estimation of soil texture, the proportions of sand, silt, and clay in a soil sample. This disclosure provides an inexpensive method of determining soil texture using a prediction model. Also provided is an inexpensive method of determining water-holding capacity and soil quality. The water-holding capacity of soil is a measurement of the amount of water the soil can retain. Knowledge of this hydrologic property may impact decisions that agronomists, producers, or farm managers make throughout the year. Water-holding capacity is determined based on knowledge of soil texture. Consequently, being able to accurately and inexpensively determine soil texture is of tremendous value for making agronomic decisions. Further soil texture, in turn, is related to soil quality which can be used by agronomists to interpret how the soil will perform under any given treatment or application, for example applying seeds, fertilizer, pesticide, herbicide, or otherwise not mentioned.

In one embodiment, the soil texture prediction model is trained using near-infrared spectroscopy (NIRS) benchmark test data and collected spectra of soil samples for which the benchmark test data has been collected. to help facilitate the prediction model of the soil properties for use with PTFs to predict soil hydrologic properties.

BRIEF DESCRIPTION OF DRAWINGS

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

The details of the present invention as a method, may be garnered in part by study of the accompanying drawings, in which the figures are referred to in numerals and is as follows.

DETAILED DESCRIPTION

Overview

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs running on computing devices, generally including a computer processor configured to operate instructions stored within a non-transitory computer readable storage medium. The instructions may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The following description provides a mechanism for determining soil texture (ST) at a sub-field level of geographic specific, and sufficiently inexpensively on a per-sample basis to allow an end-user, such as a farmer or agronomist, to cost-effectively incorporate soil texture data into their agronomic plans. This is not feasible from a business perspective with existing methods. The result of the system and method described herein is a scalable process that can allow, for example, for thousands of soil samples processed and analyzed per day, processing the equivalent of tens of thousands (e.g., 80,000 to 120,000) of acres per day of analytical throughput. Existing processes tend to cost upwards of $30 per sample to determine soil texture or other derived properties. Processing 100,000 samples at that cost for a typical field is financially infeasible. By contrast, the system and process described herein can lower that cost to approximately $1 per sample, resulting in significant savings for farmers.

Soil texture strongly influences a soil's water holding capacity. Water holding capacity is a soil's ability to hold water. Knowledge of a field's water-holding capacity can help inform an end-user's decisions on both dry-land (precipitation-dependent) farming, as well as farming under irrigation. Making soil texture data more easily available allows end users to develop improved crop, nutrient, and other plans. These plans, which are commonly tagged with the moniker "precision agriculture," generally include sets of tasks or actions to be performed at the sub-field level, for example describing dynamic nutrient prescriptions to be applied as a function of geographical position within the field.

As the system and method described herein generally lower the cost of obtaining soil texture data, this allows increasingly granular precision agriculture plans to be developed, where granularity refers to the geographical distance between soil texture determinations and/or locations where such precision agriculture plans would vary between such locations. Consequently, soil texture across a field can be comprehensively represented as an additional decision-making layer of data, which is used in conjunction with other layers of data as part of an agronomic plan.

Use of the soil texture and other layers of agronomic data may be used in a variety of ways. In one embodiment, the soil texture data layer may be incorporated into a laboratory fertility recommendation system. Fertilizer rates can be optimized depending on the soil texture. As one example, soils that possess a lighter texture would receive a recommendation with lower phosphate amounts. Typically, lower textured soils allow for a greater phosphate mobility, whereas heavier textured soils hold more springtime moisture. This attribute greatly affects yield (more water translating to a greater yield), and the greater the yield (in most crops) requires more nitrogen fertilizer to achieve the full yield potential. In another embodiment, an agronomist may directly use the soil texture data layer, or some derived layer of related data such as a water holding capacity data layer to interpret and perform their own analysis. In another embodiment, the soil texture data layer may be used as an input to an automated agronomic decision support system. Expanding the lab's recommendation system to accommodate a more intensive management system (such as FarmCommand™) as it provides a holistic management recommendation system that combines several layers of input (e.g., meteorological data, fertility, planting, imagery, planting, harvesting, and so on) would benefit from soil texture data collected to use as an additional layer, or input for the system.

Generally, the system and method produce accurate and reliable soil texture measurements of mineral soils by collecting near-infrared spectroscopic spectra of soil samples, and processing the collected spectra through a prediction model, herein referred to as the soil texture prediction model, to generate an estimate of soil texture for the soil sample. The system and method may further include derivation of other properties of the soil.

The Soil-Plant-Air-Water (SPAW) model generated by Saxton/Rawls/Willey was clearly defined in the article "Using the Soil Water Characteristic Estimates by Texture and Organic Matter for Hydrologic Solutions" by K. E. Saxton and W. J. Rawls, published in Soil Sci. Soc. AM J. 70:1569-1578 (2006). Soil and Water Management & Conservation, Soil Physics doi: 10.2136/assaj2005.0117. The SPAW model predicts: texture class, permanent wilting point, field capacity, saturation point, available water, saturated hydraulic conductivity, and bulk density.

Other examples of properties that may be derived from the soil texture estimate include, but are not limited to hydrological properties such as soil water-holding capacity, as well as non-hydrological properties such as soil class, which describes the suitability of the soil for growing specific crops.

Model Structure and Training

As introduced above, the prediction model takes an input of near infrared spectra (NIRS) collected from a soil sample and outputs a soil texture estimate comprising percentage composition of clay and sand; or silt and sand; in the soil sample. The prediction model itself comprises one or more mathematical functions and a set of learned weights, coefficients, critical values, or any other similar numerical or categorical parameters that together convert the input spectra into an estimate of soil texture. These may also be referred to as "calibration equations" for convenience. Depending on the embodiment, each such calibration equation may refer to the equation for determining the contribution of one of sand, silt, and clay, or some other arrangement of equations may be used.

In order to train the model and determine the values for the model parameters (i.e., for the calibration equations), NIR spectra for "training" soil samples are collected as inputs training for the model. Further, benchmark methods are used to obtain accurate values of the actual (true) soil texture for the soil samples. Collectively these training soil sample NIR spectra and benchmark soil texture values may be referred to as a calibration set. The parameters of the prediction model are determined by inputting the function, the training soil spectra, and corresponding true values into a supervised machine learning algorithm.

In one embodiment, either the spectra themselves or a derivative of the spectra are used to train the model. Generally, the spectra consist of intensities of light over a range of wavelengths in the near infrared range. Depending on the relative proportion of sand, silt, and clay in a sample, different spectra will be produced. Even for any given component (i.e., sand, silt, and clay) the spectra (or first derivative thereof) generated by different samples will vary. The model encodes the latent properties of soil that cause these varying spectra.

The type of modelling function may vary by implementation. In one embodiment, regression techniques such as ElasticNet, linear, logistic, or otherwise may be used. Other techniques may also be used, examples of which include Random Forest Classifiers, Neural Nets, Support Vector Machines, and so on. The model in this example used the partial least squares method.

The prediction model may have several different outputs, depending on the implementation. One implementation may generate a prediction for the presence, relative or absolute, of each of sand, silt, and clay within the soil sample. Another implementation may generate a prediction for the presence of two of the three (e.g., sand and silt but not clay) and then derive the proportion of the third (e.g., clay) by subtracting the proportional presences of sand and silt from 100%, under the assumption that these three materials make up 100% of the composition of the soil. Any permutation is within the scope of this disclosure with respect to which two materials are directly predicted and which material is derived based on the relative presence of the other two.

Once trained, the resulting prediction model can then be used to predict the soil textures of unknown mineral soils. Generally, the prediction model is able to handle both soil samples collected from the surface as well as soil samples (surface soil samples) collected deeper below the surface (sub-surface soil samples). Generally, soil texture does not vary significantly between surface soil and subsurface soil. That said, differences in silt, clay, and sand content between surface samples and subsurface samples can be evaluated. For example, statistical correlation of the measured sand and clay in the calibration set versus the soil texture values predicted by the prediction model may be greater in the calibration set for the subsurface samples as compared to the surface samples. This effect may be attributed to differences in the composition of surface and subsurface soil. This difference may be used to numerically compute an uncertainty measure for the predicted sand and clay values generated by the prediction model. This may provide along with the predicted soil texture or any derived quantities as indicative of the relative accuracy and/or precision of the prediction.

To obtain the NIR spectra for either the training soil samples or unknown soil samples, the spectra can be generated using a Bruker Matrix-I NIRS spectrometer or a Bruker HTS 250 auto-sampler, or another similar device.

Use of Calibration Equations

The soil textures predicted by the calibration equations can be used to predict other properties of the soil. As one example, hydrologic properties of the soil are deduced by applying the soil's sand, silt and clay content as predicted by the model and a separate measure of SOM and electrical conductivity to a PTF to generate an output measurement of a hydrological property such as water holding capacity. Generally, any of several PTFs may be applied to the soil texture estimate provided by the model to derive any of a number of hydrological properties, examples of which include, but are not limited to field capacity (FC), saturation (Sat), permanent wilting point (PWP), and plant available water (PAW). In one embodiment, the PTF is calibrated to the geographical region in which the soils are found. Often, geographical regions have different soil properties from each other, such as the difference between Midwest United States soil and Canadian Northwest soil.

In one embodiment, Saxton and Rawls (Soil Water Characteristics Estimates by Texture and Organic Matter for Hydrologic Solutions) can be the basis for estimating soil hydrologic characteristics using the predictions output by the prediction model (e.g., sand and clay predictions for the spectra collected by the NIRS). The following equations provide examples of how Sand (S), and Clay (C) predictions may be used along with an Organic Matter (OM) measurement to calculate a number of hydrologic characteristics of a soil sample.

Equation Summary for Soil Water Characteristic Estimates

| Variable | Equation | $R^2/S_e$ | Eq. |
|---|---|---|---|
| | Moisture Regressions | | |
| $\theta_{1500}$ | $\theta_{1500} = \theta_{1500t} + (0.14 \times \theta_{1500t} - 0.02)$<br>$\theta_{1500t} = -0.024S + 0.487C + 0.006\ OM + 0.005\ (S \times OM) - 0.013(C \times OM) + 0.068\ (S \times C) + 0.031$ | 0.86/0.02 | 1 |
| $\theta_{33}$ | $\theta_{33} = \theta_{33t} + [1.283(\theta_{33t})^2 - 0.374(\theta_{33t}) - 0.015]$<br>$\theta_{33t} = -0.251S + 0.195C + 0.011OM + 0.006(S \times OM) - 0.027(C \times OM) + 0.452(S \times C) + 0.299$ | 0.63/0.05 | 2 |
| $\theta_{(S-33)}$ | $\theta_{S-33} = \theta_{(S-33)t} + (0.6360(_{S-33t}) - 0.107)$<br>$\theta_{(S-33)t} = 0.278S + 0.034C + 0.022OM - 0.018(S \times OM) - 0.027(C \times OM) - 0.584(S \times C) + 0.078$ | 0.36/0.06 | 3 |
| $\psi_e$ | $\psi_e = \psi_{et} + (0.02\psi^2_{et} - 0.113\psi_{et} - 0.70)$<br>$\psi_{et} = -21.67S - 27.93C - 81.97\theta_{S-33} + 71.12(S \times \theta_{S-33}) + 8.29(C \times \theta_{S-33}) + 14.05(S \times C) + 27.16$ | 0.78/2.9 | 4 |

-continued

| Variable | Equation | $R^2/S_e$ | Eq. |
|---|---|---|---|
| $\theta_S$ | $\theta_S = \theta_{33} + \theta_{(s\text{-}33)} - 0.097S + 0.043$ | 0.29/.04 | 5 |
| $\rho N$ | $\rho N = (1 - \theta_S)2.65$ | | 6 |
| | Density Effects | | |
| $\rho DF$ | $\rho DF = \rho N \times DF$ | | 7 |
| $\theta_{(S\text{-}DF)}$ | $\theta_{S\text{-}DF} = 1 - (\rho_{DF}/2.65)$ | | 8 |
| $\theta_{33\text{-}DF}$ | $\theta_{33\text{-}DF} = \theta_{33} - 0.2(\theta_S - \theta\ S\text{-}DF)$ | | 9 |
| $\theta_{(S\text{-}33)DF}$ | $\theta_{(S\text{-}33)DF} = \theta_{S\text{-}DF} - \theta_{33\text{-}DF}$ | | 10 |
| | Moisture-Tension | | |
| $\psi_{(1500\text{-}33)}$ | $\psi_\theta = A(\theta)^{-B}$ | | 11 |
| $\psi_{(33\text{-}\psi)}$ | $\psi_\theta = 33.0 - [(\theta - \theta_{33})(33.0 - \psi_e)/(\theta_S - \theta_{33})]$ | | 12 |
| $\psi_{(\psi\text{-}0)}$ | $\theta = \theta_S$ | | 13 |
| A | $A = \exp(\ln 33 + B\ln\theta_{33})$ | | 14 |
| B | $B = [\ln(1500) - \ln(33)]/[\ln(\theta_{33}) - \ln(\theta_{1500})]$ | | 15 |
| | Moisture-Conductivity | | |
| $K_S$ | $K_S = 1930(\theta_S/\theta_{33})^{(3-\lambda)}$ | | 16 |
| $K_\theta$ | $K_\theta = K_S(\theta/\theta_S)^{[3+(2/\lambda)]}$ | | 17 |
| $\lambda$ | $\lambda = 1/B$ | | 18 |
| | Gravel Effects | | |
| $R_v$ | $R_v = (\alpha R_w)/[1 - R_w(1 - \alpha)]$ | | 19 |
| $\rho B$ | $\rho B = \rho_N(1 - R_v) + (R_v \times 2.65)$ | | 20 |
| $PAW_B$ | $PAW_B = PAW(1 - R_v)$ | | 21 |
| $K_b/K_s$ | $K_b/K_s = \dfrac{1 - R_w}{[1 - R_w(1 - 3\alpha/2)]}$ | | 22 |
| | Salinity Effects | | |
| $\psi_0$ | $\psi_0 = 36EC$ | | 23 |
| $\psi_{0\theta}$ | $\psi_{0\theta} = \dfrac{\theta_S}{\theta}(36EC)$ | | 24 |

Symbol definitions for the equations above are provided below:

| Symbol | Definition |
|---|---|
| A, B | Coefficients of moisture-tension, Eq. [11] |
| C | Clay, % w |
| DF | Density adjustment Factor (0.9-1.3) |
| EC | Electrical conductance of a saturated soil extract, dS m$^{-1}$ (dS/m = milli-mho cm$^{-1}$) |
| FC | Field Capacity moisture (33 kPa) % v |
| OM | Organic Matter, % w |
| PAW | Plant Avail. Moisture (33-1500 kPa, matric soil), % v |
| $PAW_B$ | Plant Avail. Moisture (33-1500 kPa, bulk soil), % v |
| S | Sand, % w |
| SAT | Saturation moisture (0 kPa), % v |
| WP | Wilting point moisture (1500 kPa), % v |
| $\theta_\psi$ | Moisture at tension, $\psi$, % v |
| $\theta_{1500t}$ | 1500 kPa moisture, first solution, % v |
| $\theta_{1500}$ | 1500 kPa moisture, % v |
| $\theta_{33t}$ | 33 kPa moisture, first solution, % v |
| $\theta_{33}$ | 33 kPa moisture, normal density, % v |
| $\theta_{33\text{-}DF}$ | 33 kPa moisture, adjusted density, % v |
| $\theta_{(S\text{-}33)t}$ | SAT-33 kPa moisture, first solution, % v |
| $\theta_{(S\text{-}33)}$ | SAT-33 kPa moisture, normal density, % v |
| $\theta_{(S\text{-}33)DF}$ | SAT-33 kPa moisture, adjusted density, % v |
| $\theta_S$ | Saturated moisture (0 kPa), normal density, % v |
| $\theta_{S\text{-}DF}$ | Saturated moisture (0 kPa), Adjusted density, % v |
| $\psi_\theta$ | Tension at moisture $\theta$, kPa |
| $\psi_{et}$ | Tension at air entry, first solution, kPa |
| $\psi_e$ | Tension at air entry, (bubbling pressure), kPa |
| $K_S$ | Saturated conductivity (matric soil), mm h$^{-1}$ |
| $K_B$ | Saturated conductivity (bulk soil), mm h$^{-1}$ |
| $K_\theta$ | Unsaturated conductivity at moisture $\theta$, mm h$^{-1}$ |
| $\rho N$ | Normal density, g cm$^{-3}$ |
| $\rho B$ | Bulk soil density (matric plus gravel), g cm$^{-3}$ |
| $\rho DF$ | Adjusted density, g cm$^{-3}$ |
| $\lambda$ | Slope of logarithmic tension-moisture curve |
| $\alpha$ | Matric soil density/gravel density (2.65) = $\rho/2.65$ |
| Rv | Volume fraction of gravel (decimal), g cm$^{-3}$ |
| Rw | Weight fraction of gravel (decimal), g g$^{-1}$ |
| $\psi_0$ | Osmotic potential at $\theta = \theta_s$, kPa |
| $\psi_{\theta 0}$ | Osmotic potential at $\theta < \theta_s$, kPa |

Sample Preparation

Figure 1:
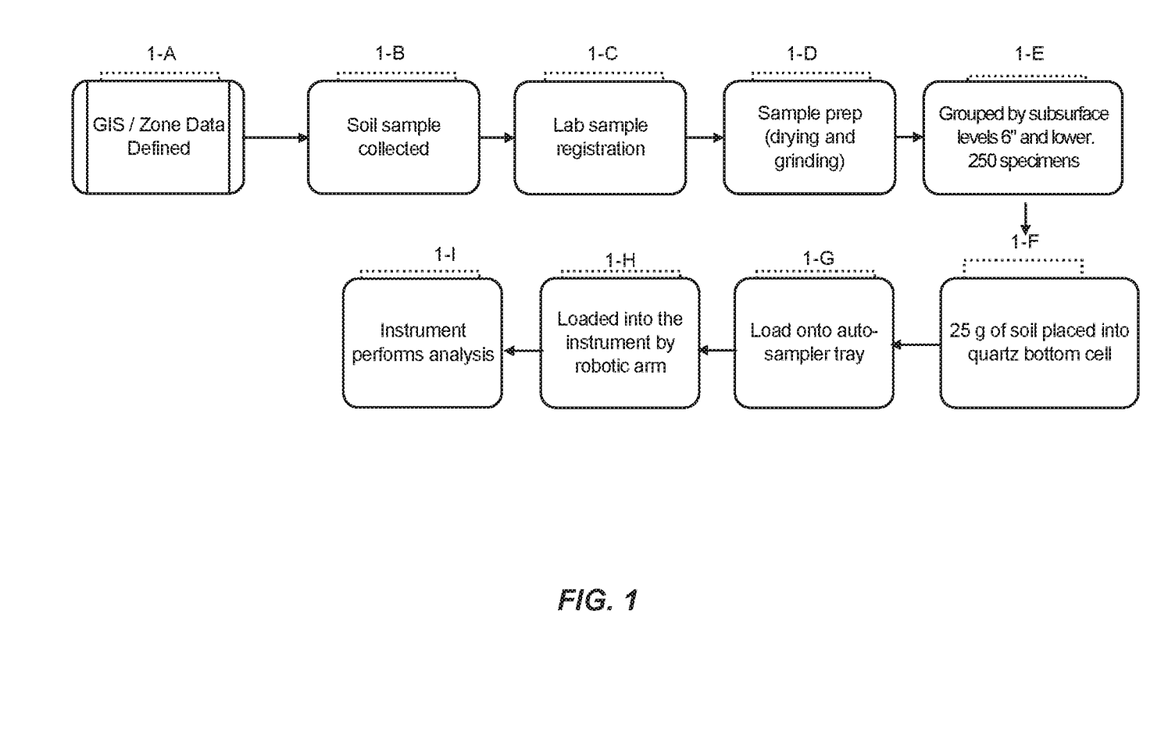
FIG. 1 is a flow diagram of an example method for preparing soil samples for NIRS analysis, according to one embodiment.

FIG. 1 is a flow diagram of an example method for preparing soil samples for NIRS analysis, according to one embodiment. Geographic Information System (GIS) image data is collected through the satellite imagery. The GIS images are used to identify field zones, 1-A. An accumulation of all the zones within a field are used to define a zone map. Once the map is approved, soil samples are collected from each pre-selected zone that a soil sample is to be collected from, 1-B. The density of soil sample collection may vary based on the needs of the collector, but generally due to the decreased cost of this process, higher densities of soil sampling may be achieved at lower cost relative to existing processes. The samples are received at a lab, registered with identifying information, and processed into the system, 1-C. Once the soil sample is logged and registered, the soil is prepared for analysis, for example for processing by a Bruker Matrix-I NIRS, 1-D. Preparation of the soil includes drying and dehydrating to prevent soil reaction. The soil is pulverized into homogenous samples. Once the soil is prepared, samples (e.g., 250) are collected from six inches or lower of subsurface soil, 1-E. From each soil sample, some portion of that soil sample (e.g., twenty-five grams) is placed into the device, such as into quartz bottom cells of the Bruker device mentioned above, 1-F, and loaded onto the auto-sampler tray 1-G. The samples may be loaded into the instrument automatically by the robotic arm, 1-H. The machine generates the spectra, 1-I.

Spectra Collection

Figure 2:
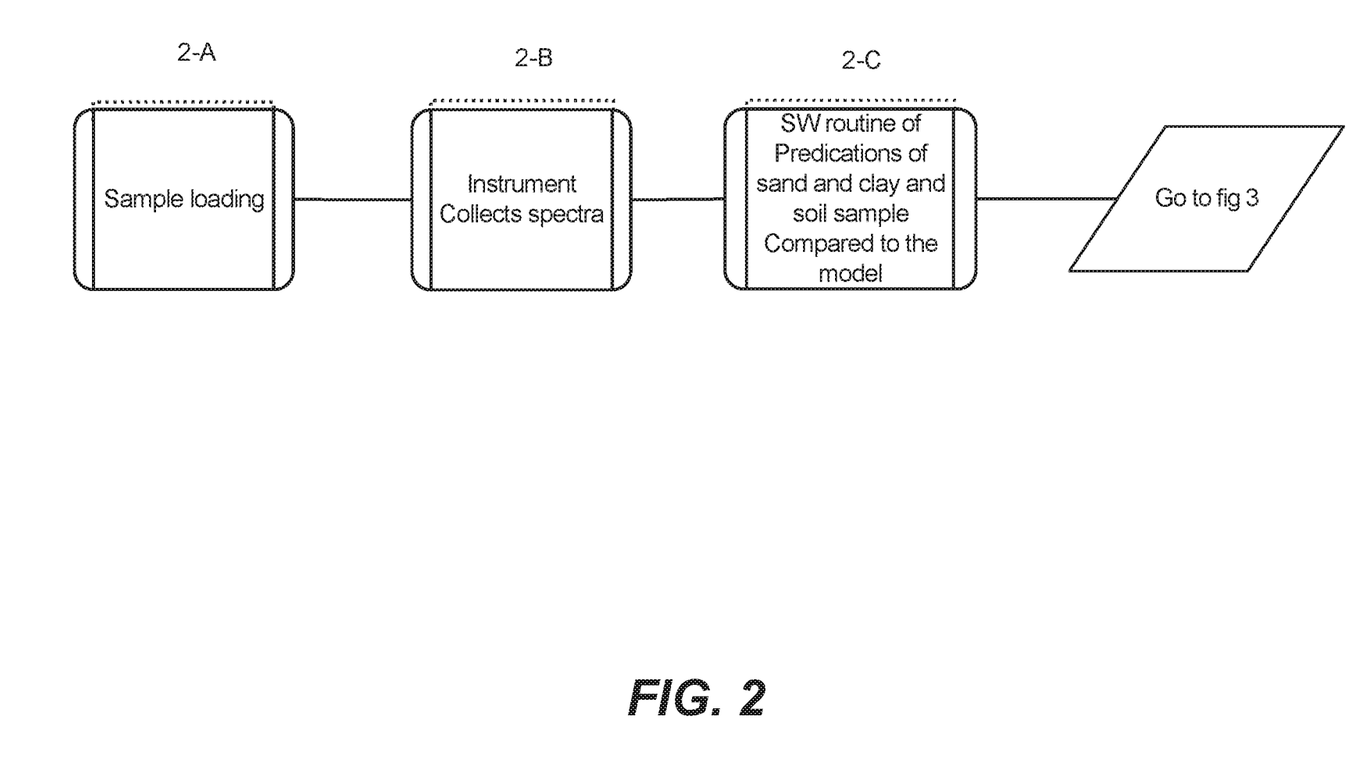
FIG. 2. is a flow diagram of an example method for performing NIRS analysis and using the output soil spectra as an input to a soil texture prediction model to estimate soil texture, according to one embodiment.

FIG. 2. is a flow diagram of an example method for performing NIRS analysis and using the output soil spectra as an input to a soil texture prediction model, according to one embodiment. After the samples are loaded, 2-A, the samples are scanned, 2-B. In one embodiment, spectral resolution is set to 16 reciprocal centimeters (16 cm$^{-1}$), samples are scanned 32 times, as well as 32 background scans. In one embodiment, spectral range is defined 12,500 cm$^{-1\circ}$ to 3,600 cm$^{-1}$. In the Bruker device, spectra are collected with rotating sample presentation. In one embodiment, the device uses an Fourier Transform Apodization function with a Blackman-Harris 3-Term. A combination of treatments is applied to the spectra collected and that is specific for the region (e.g., spectra benchmark defined for the Canadian prairies will be different than spectra collected from the US Midwest). The collected spectra for each sample is then output for insertion into the prediction model, 2-C. Although a particular method for performing NIRS analysis has been described in this paragraph, one of skill in the art will understand that different spectrometer settings and scan techniques and settings may be used to obtain similar NIR spectra that are within the scope of this description.

Soil Texture Prediction

Figure 3:
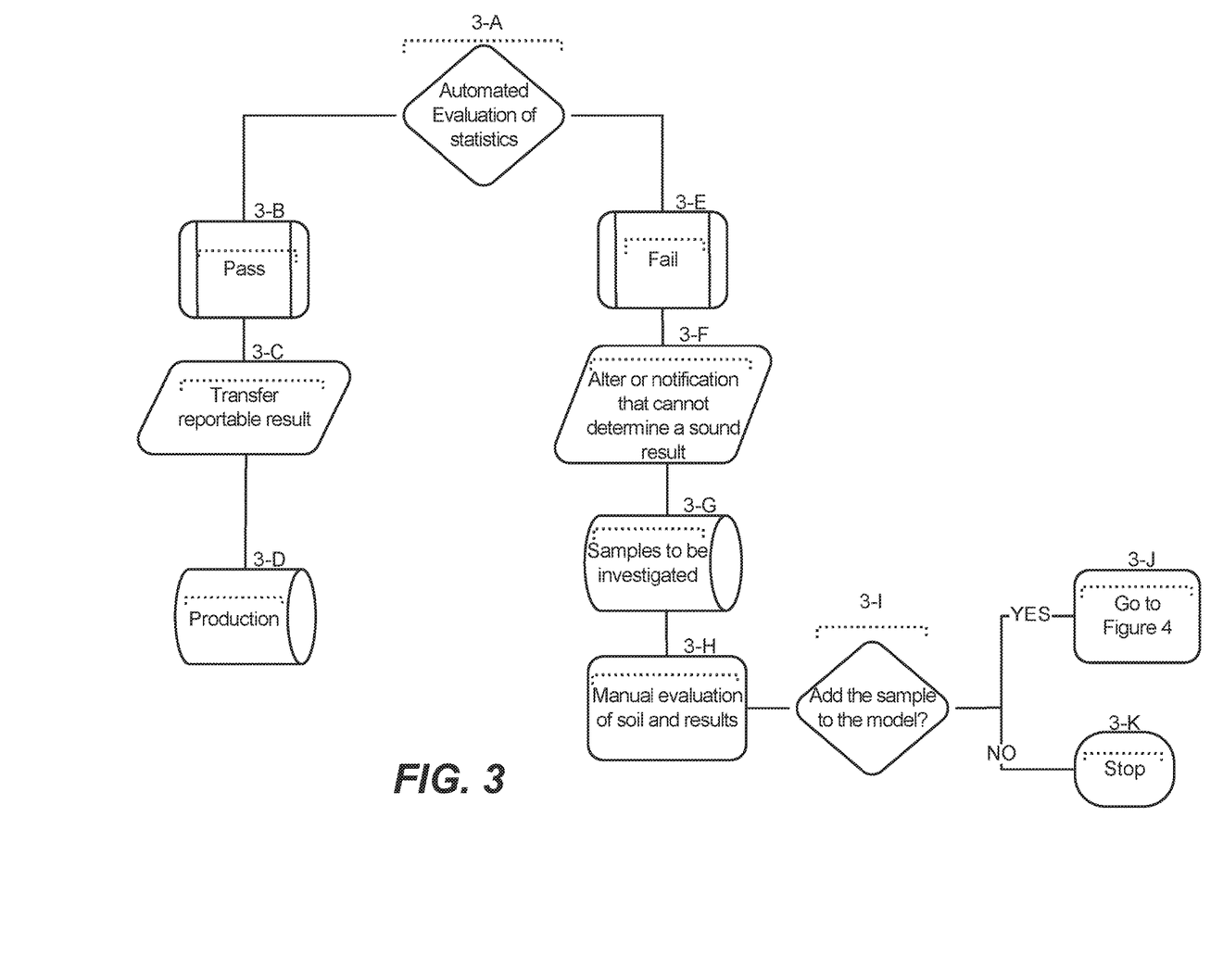
FIG. 3 is a flow diagram of an example method for evaluating the output of the soil texture prediction model that includes steps for determining whether to use evaluated soil samples to improve on a trained soil texture prediction model, according to one embodiment.

FIG. 3 is a flow diagram of an example method for evaluating the output of the soil texture prediction model that includes steps for determining whether to use evaluated soil samples to improve on a trained soil texture prediction model, according to one embodiment. In addition to generating an estimate of soil texture, the prediction model may be further configured to generate a determination as to whether the collected spectrum lies within the statistical confidence of the NIRS calibrated model, i.e., whether the prediction has "passed" or "failed", 3-A. The sample result spectra is compared to that of the calibration spectra, if the results align within the statistical confidence of the model's calibration, the result is considered "pass". Should the result from the collected sample fall outside the statistical confidence of the model's calibration, the result is identified as "fail". Should the results pass, 3-B, the reportable result is transferred, 3-C, to a production database where soil texture results may, among other things, be made available to the submitter 3-D. Whereas if the result is a "fail", 3-E, an automated alert or notification indicating that the result of the sample either failed or no prediction was made to the submitter and/or to the administrator of the prediction model, 3-F. Failed results are also stored in a database, 3-G. Further investigation on the fail results requires a manual evaluation, 3-H, and a determination whether the soil sample that failed should be added to the model as another training soil sample, 3-I. The investigation is a manual review of the sample. If the decision is to add the soil sample result to the model, 3-J then the process for analyzing training samples as discussed above and with respect to FIG. 4 below is performed. If the decision is not to add the soil sample to the model, in 3-K, it is discarded. A good example of a sample that should not be added to the model would be soil samples that are non-mineral or largely non-mineral in nature.

Processing Training Soil Samples

Figure 4:
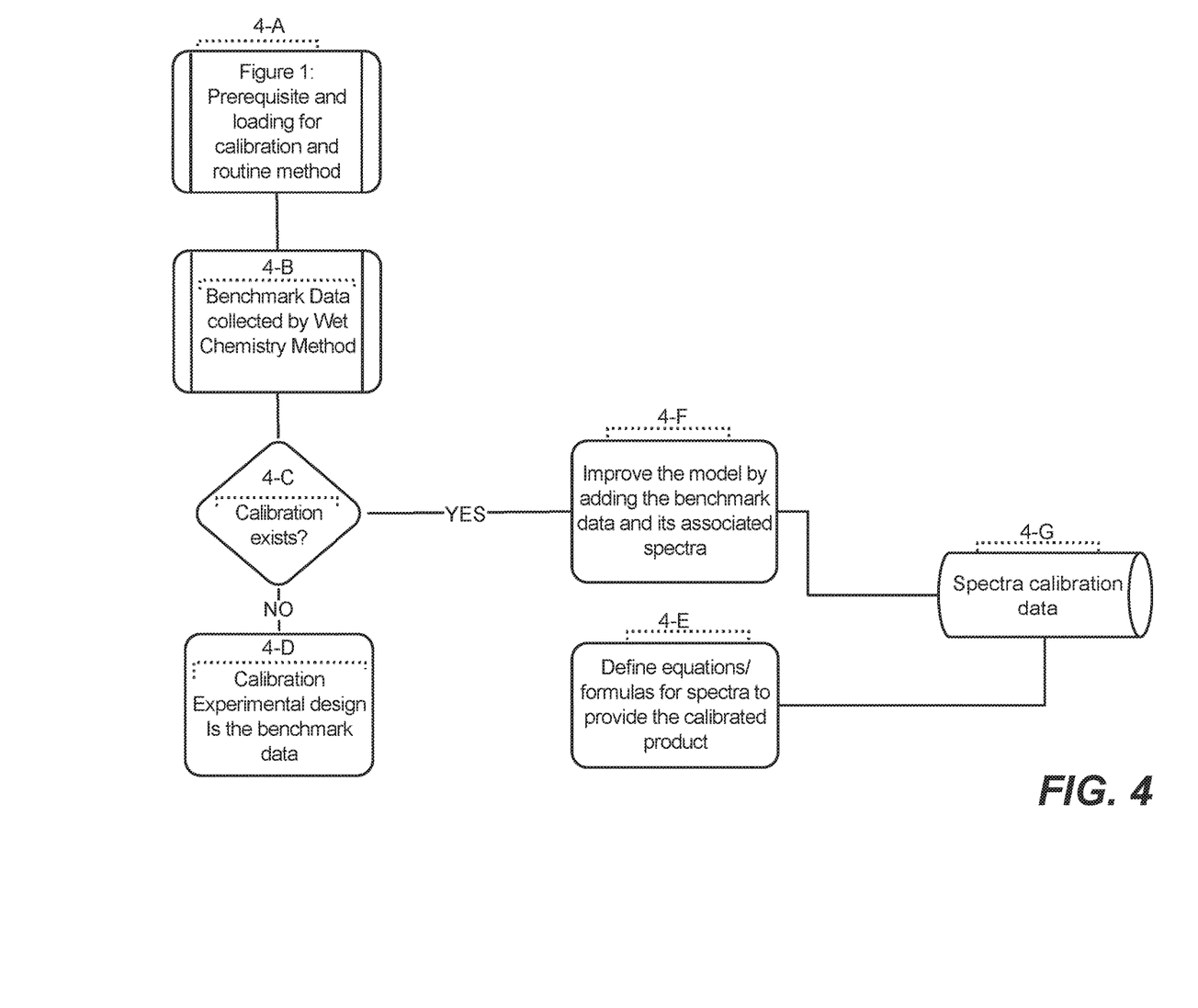
FIG. 4 is a flow diagram of an example method for training a soil texture prediction model, according to one embodiment.

FIG. 4 is a flow diagram of an example method for training a soil texture prediction model, according to one embodiment. A process for preparing test soil samples is performed, at 4-A. This may, for example, be the example process of FIG. 1, however other similar processes may also be performed. The benchmark soil texture data may be collected by a wet chemistry method, 4-B. The benchmark soil texture data collected becomes the dataset of collected samples, which in turn is used for the model's computation. Should the values exist in the dataset, 4-C, the spectra is processed through the model and a prediction is given. The prediction is accomplished by relating the values from the two datasets, i.e. the collected sample and the existing pool of benchmark data, by way of applying mathematical treatments within the model. Processing algorithms are optimized in the iterative stepping set the pre-processing and then set the ranges, and then select the optimization. Best fit throws the treatments from the wizard, set the treatment and validation. Permutations, regions, and then results are ranked. Outliers of data, that is the statistical output outlier. If the calibration exists, then the model is improved by the addition of the new benchmark data and its associated spectra, 4-F. Then the data is added to the calibration data set in the spectra calibration data, 4-G. If the calibration does not exist in the model, 4-D, then the calibration experimental design is the benchmark data. Defined equations and formulas for spectra to provide the calibrated product 4-E and then added to the spectra calibration database. In one example implementation, collected spectral data is stored in a relational database for further analysis and re-prediction with subsequent calibrations.

To determine benchmark values of soil texture for the training soil samples, any one of a number of known techniques may be used. For example, to determine the proportion of clay in a training soil sample sedimentation may be performed using a hydrometer. In sedimentation, the soil sample is put into suspension, and after a duration the amount of clay still in solution is measured after the sand and silt have fallen out of suspension. As another example, to determine the proportion of sand in a training soil sample, wet sieving may be performed. In one example, a sieve of aperture size 53 micrometers is used. Other techniques may also be such as the pipette method for clay or laser diffraction, where appropriate. In one embodiment, sand and clay are measured, and silt is measured by taking the total of sand and clay and finding the difference from the total soil content. Silt is inferred by taking a 100% of the soil content and subtracting the percentage of sand, and subtracting the percentage of clay, leaving the percentage value of silt. (e.g., 100%−x % sand−x % clay=% silt).

Examples

Figure 5:
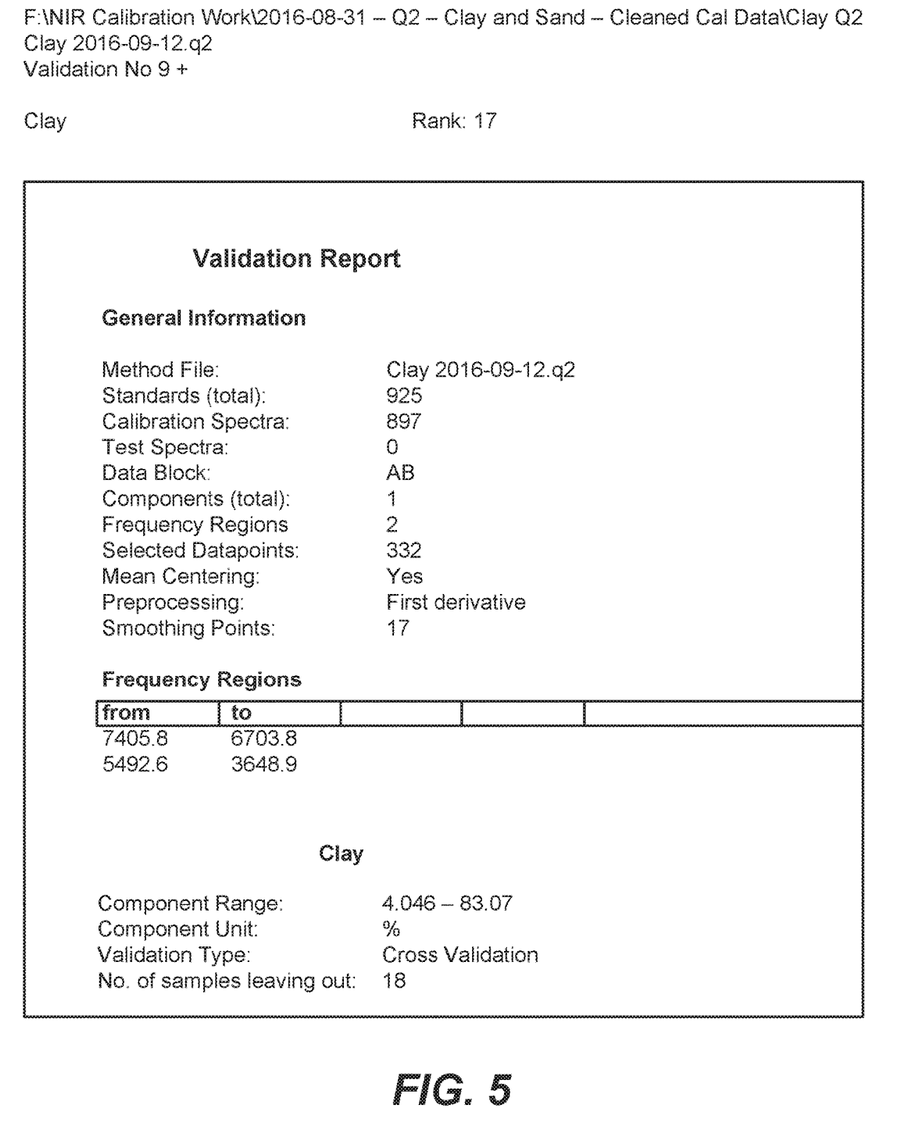
FIG. 5 is an example of a clay and sand summary page of a clay validation report, according to one embodiment.

FIG. 5 is an example of a clay and sand summary page of a clay validation report, according to one embodiment. This is a summary overview with administrative data on the sample and the method used by the spectra that is generated by the instrument. The summary includes a snapshot into the sample that was collected. The method that the model used is identified under the "General Information", "Method file Clay 2016-09-12.q2". The method used for this instance was partial least squares. The value provided in the "Standards (total)" represents the total number of records that the instrument has validated for the model. Whereas as the "Calibration spectra" value is the representation of records within the dataset that was used by the model. "Rank" represents how many factors were applied to the spectral features. Factors are the eigenvectors of the sample concentration matrix and the eigenvectors of the corresponding spectral matrix. The spectral matrix has a number of rows based on the number of training soil samples used to train the soil texture prediction model, and columns for each spectral value (or for each binned range of spectral values). The sample concentration matrix has a number of rows based on the number of training soil samples used to train the soil texture prediction model, and columns for each sample concentration value, or range of concentration values.

In the example embodiment of FIG. 5, the soil texture prediction model is trained using partial least squares (PLS) regression which identifies, for a given function, the coefficients that best (according to PLS error) correlate the eigenvectors of the sample concentration matrix obtained from each of a number of training samples to the eigenvectors of the spectral matrix corresponding to each of those training samples. The report will indicate the Component Range, in percent, how the validation was achieved, and how many, if any samples were left out.

Figure 6:
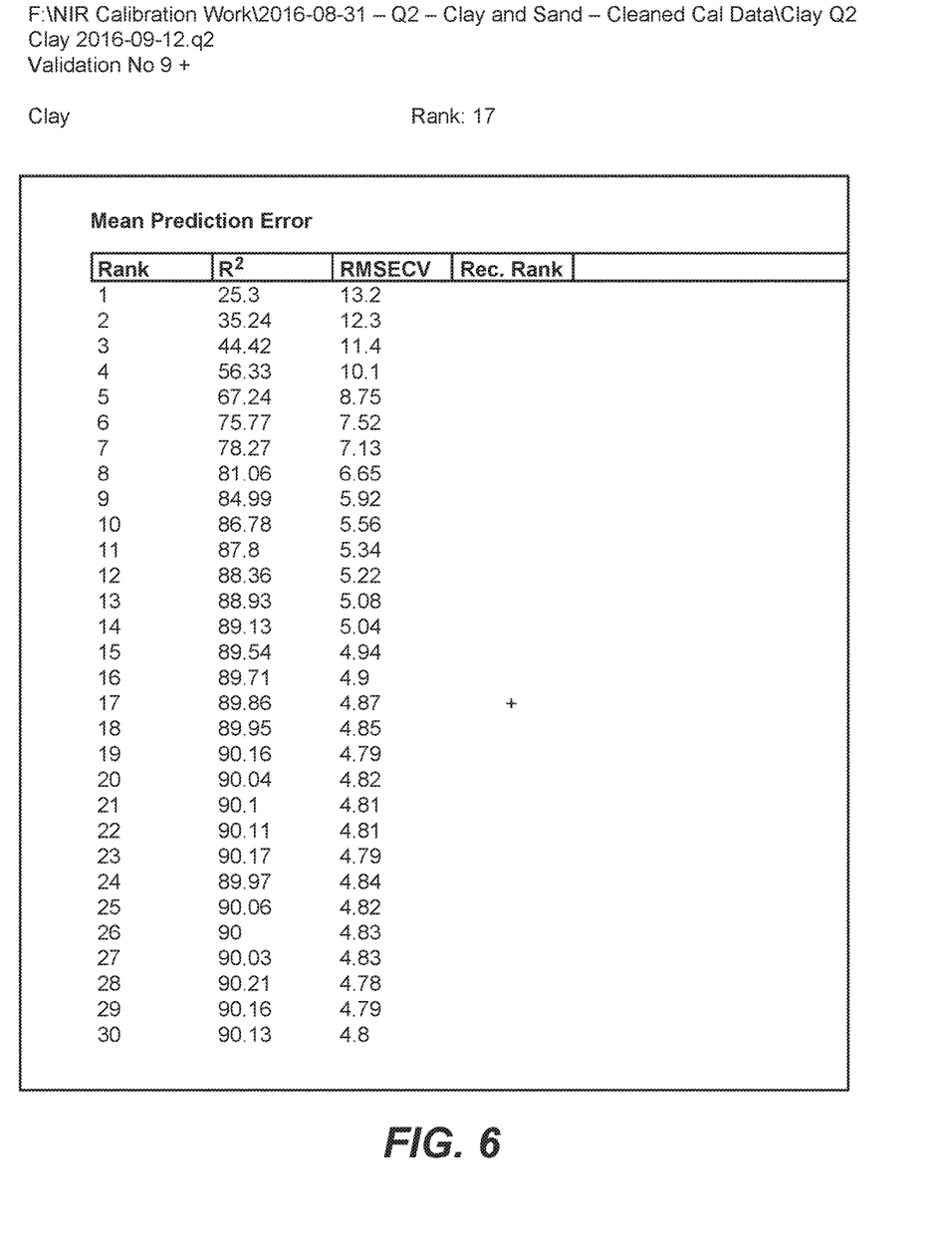
FIG. 6 is an example of the clay and sand validation report for a clay mean prediction error, according to one embodiment.

FIG. 6 is an example of the clay and sand validation report for a clay mean prediction error, according to one embodiment. Here, the rank represents how many factors were applied to the spectral features.

Figure 7:
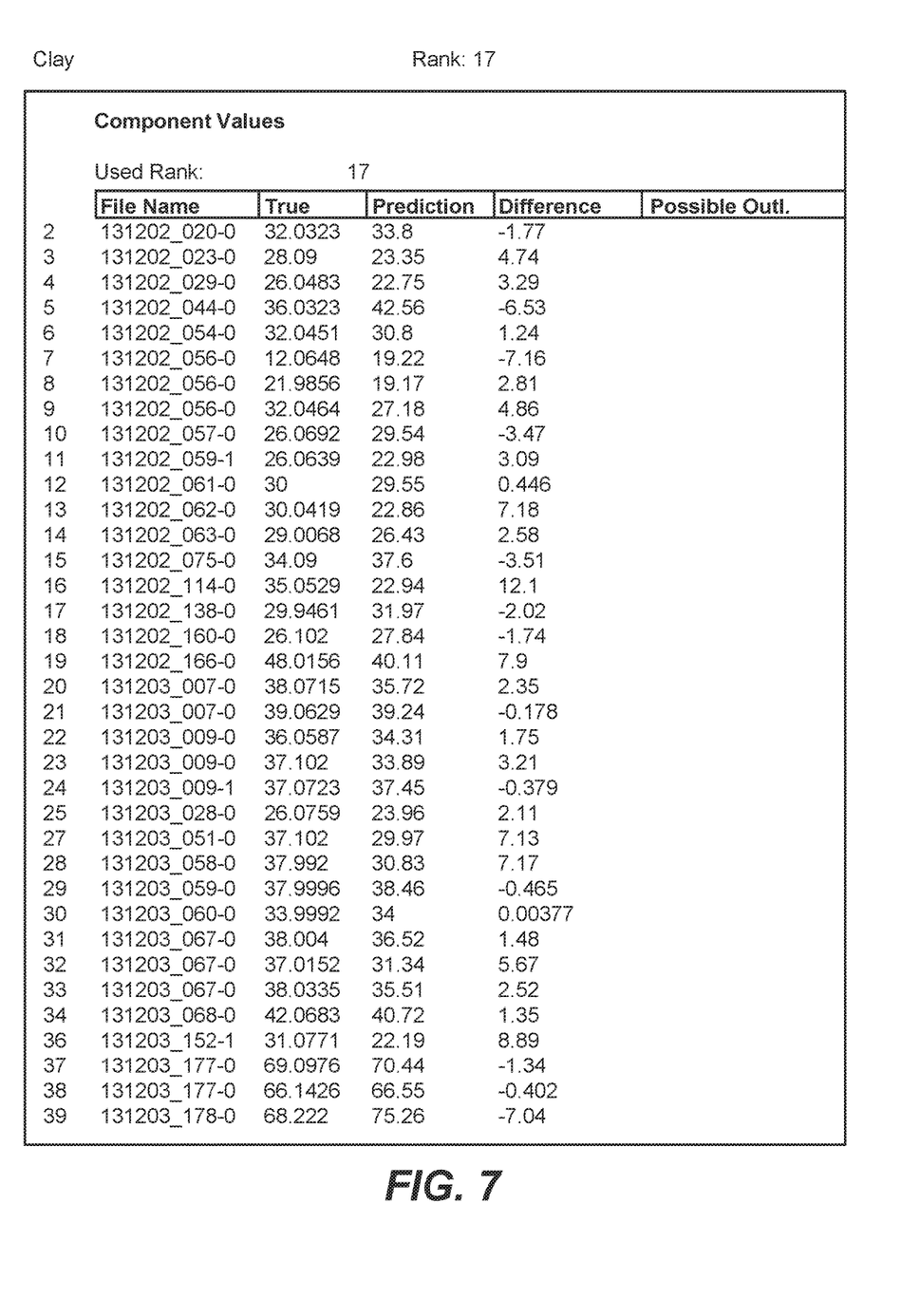
FIG. 7 is an example of the clay and sand validation report for clay component values, according to one embodiment.
Figure 8:
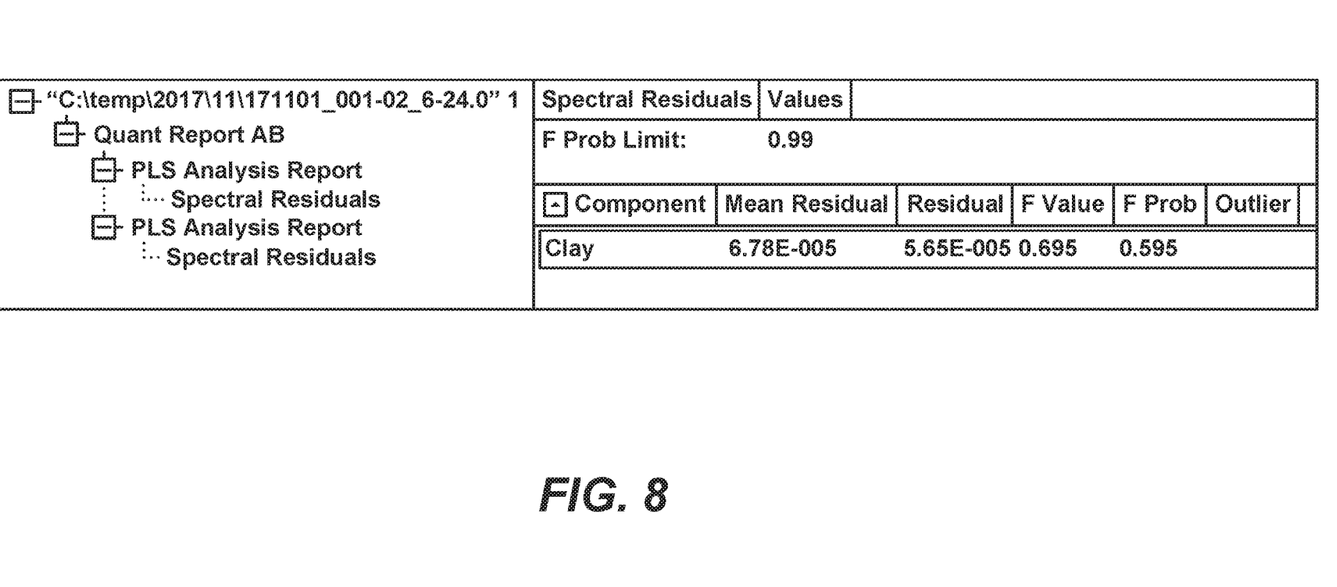
FIG. 8 is an example of prediction for clay, according to one embodiment.
Figure 9:
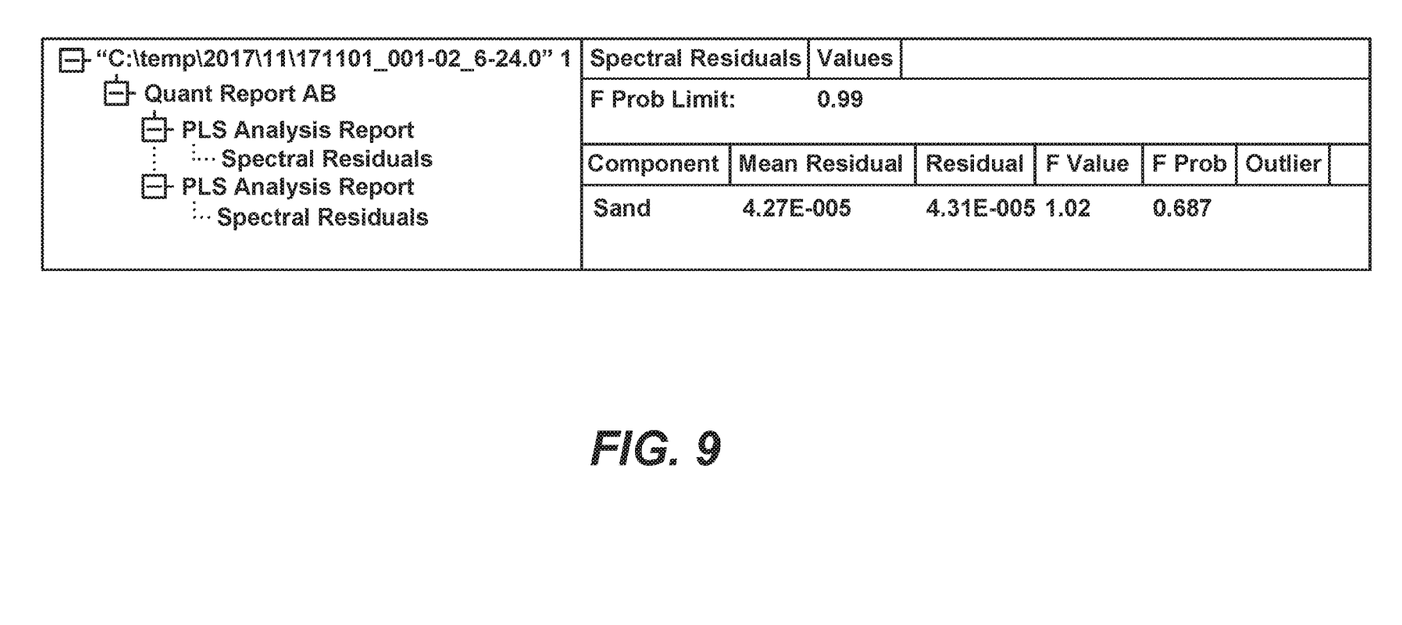
FIG. 9 is an example of prediction for sand, according to one embodiment.
Figure 10:
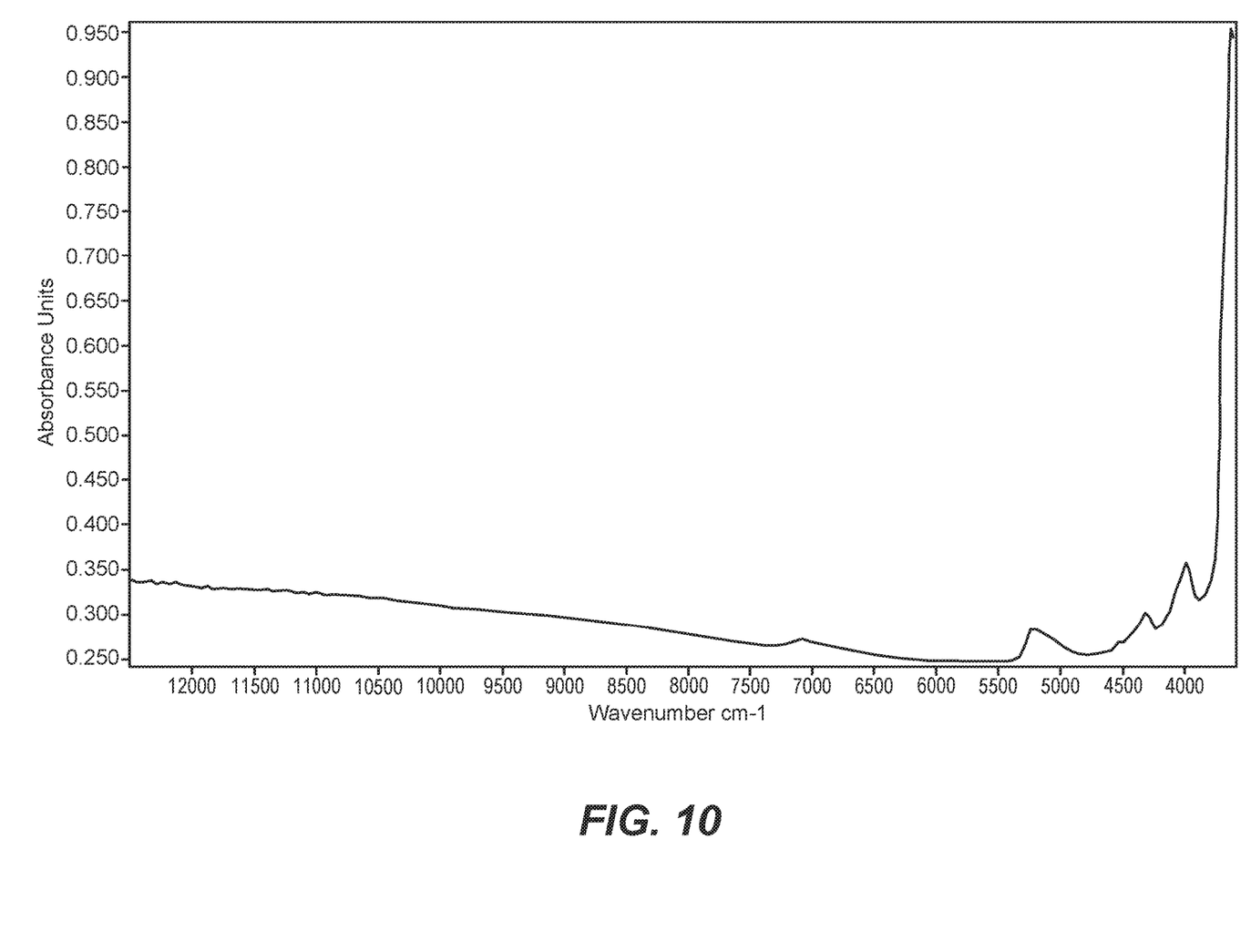
FIG. 10 is an example of a NIR spectrum, according to one embodiment.
Figure 11:
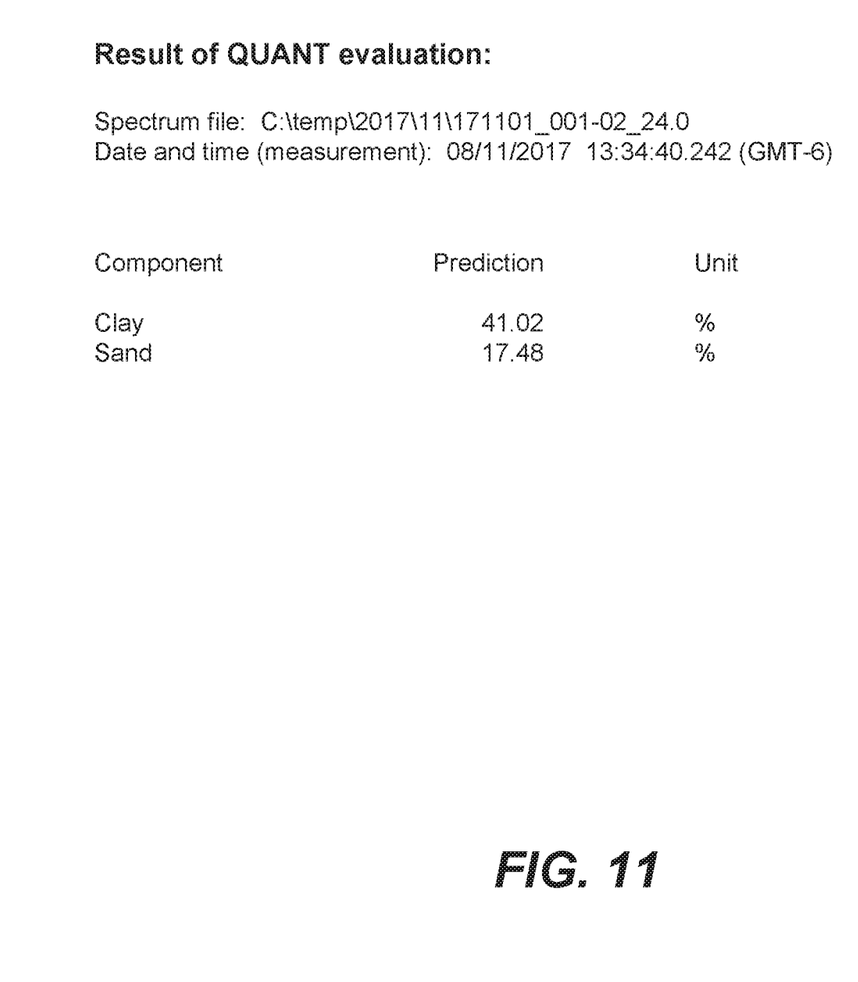
FIG. 11 is an example prediction summary, according to one embodiment.

FIG. 7 is an example of the clay and sand validation report for clay component values, according to one embodiment. The component values indicate how closely the model calculated the predication and validated against a known set of data. This example report provides a prediction on the sample, while the instrument uses the spectra collected to calibrate, it will use the spectra for the prediction. The model moves through iterations of samples, and the rank identifies how many factors were applied to each sample. Overall, the "Difference" column provides the variance between the tested value and the predicted value. A sum of the variance at the end of the report equals zero.

The predictions versus the benchmark datasets are validated by taking the test cases and relating them back to the true values of a traditional model, e.g. wet chemistry methods, in effort to validate that the model is working. Validation involves relating the predictions of the model to the true values collected that were collected. The following example table demonstrates the number of samples that were predicted in an example training model run on samples collected from the Canadian prairies during the Fall of 2017, and outlines the model's level of certainty.

The Mahalanobis outlier is identified in the "Mah out" column and represents the total count, whereas the % mah out represents the percentile. The Spectra outlier total count is represented by the Spec Out, and likewise the percentile is captured in the "% spec out" column. The Spectra outlier captures the total confidence of whether the spectra residual falls as an outlier.

|  | Count | Mah Out | Spec Out | % mah out | % spec out |
| --- | --- | --- | --- | --- | --- |
| Clay | 60803 | 2739 | 8866 | 4.504711939 | 14.58151736 |
| Sand | 60803 | 5505 | 18098 | 9.053829581 | 29.7649787 |

What is claimed is:

1. A method comprising:
receiving a soil sample;
processing the soil sample to generate a prepared soil sample, wherein processing the soil sample comprises:
(i) drying the soil sample, and
(ii) pulverizing the soil sample until the soil sample is substantially homogeneous;
analyzing the prepared soil sample with a spectrometer capable of generating spectra in a near-infrared range to generate a near-infrared spectral data set for the prepared soil sample;
inputting, with a computer, the near-infrared spectral data set into a soil texture prediction model to generate a soil texture estimate for the soil sample, the soil texture estimate comprising at least two of: a sand proportion, a silt proportion, and a clay proportion; and
providing the soil texture estimate.

2. The method of claim 1 wherein receiving the soil sample comprises:
identifying the soil sample and associating the soil sample with a geographic location.

3. The method of claim 1 wherein analyzing the prepared soil sample with the spectrometer comprises scanning the soil sample over a spectral range comprising 12,500 cm$^{-10}$ to 3,600 cm$^{-1}$.

4. The method of claim 1 wherein analyzing the prepared soil sample with the spectrometer comprises scanning a plurality of times.

5. The method of claim 1 comprising:
inputting, with a computer, the soil texture estimate into a pedotransfer function to determine a hydrological property of the soil sample.

6. The method of claim 5 wherein inputting the soil texture estimate into the pedotransfer function further comprises determining a soil organic matter content of the soil sample and inputting it into the pedotransfer function to determine the hydrological property.

7. The method of claim 6, wherein the hydrological property of the soil sample is one selected from the group consisting of: soil water-holding capacity, field capacity, high and low watermarks, saturation point, permanent wilting point, and plant available water.

8. A method comprising:
receiving a soil sample;
processing the soil sample to generate a prepared soil sample;
analyzing the prepared soil sample with a spectrometer capable of generating spectra in a near-infrared range to generate a near-infrared spectral data set for the prepared soil sample;
inputting, with a computer, the near-infrared spectral data set into a soil texture prediction model to generate a soil texture estimate for the soil sample, the soil texture estimate comprising at least two of: a sand proportion, a silt proportion, and a clay proportion, wherein the soil texture prediction model comprises a set of parameters learned using a supervised learning technique based on:
(i) labeled output data comprising benchmark soil texture estimates from previously collected training soil samples, the labeled output data indicating at least two of: a sand proportion, a silt proportion, and a clay proportion,
(ii) input data comprising near-infrared spectra for each of the training soil samples, and
(iii) a function configured to receive the near-infrared spectra for each of the training soil samples as input and together with the parameters that generate the soil texture estimate; and
providing the soil texture estimate.

9. The method of claim 8, wherein the supervised learning technique is one selected from the group consisting of: a regression, a neural network, a support vector machine, and a random forest classifier.

10. The method of claim 8, wherein the training soil samples used are processed using a same process as the processing of the soil sample.

11. The method of claim 8, wherein the benchmark soil texture estimates for the training soil samples are generated using at least one technique selected from the group consisting of a sedimentation technique, a wet sieving technique, and a pipette technique.

12. The method of claim 8, further comprising:
determining whether the soil texture estimate passes or fails a test;
responsive to the soil texture estimate failing the test, generating a new benchmark soil texture estimate for the soil sample; and
determining whether to add the soil sample and the new benchmark soil texture to the training soil samples used to determine the parameters of the soil texture prediction model.

13. The method of claim 12, wherein the test evaluates a soil organic matter content of the soil sample.

14. The method of claim 8, wherein processing the soil sample comprises:
drying the soil sample; and
pulverizing the soil sample until the soil sample is substantially homogeneous.

15. The method of claim 8, further comprising:
inputting, with a computer, the soil texture estimate into a pedotransfer function to determine a hydrological property of the soil sample.

16. A method comprising:
receiving a soil sample;
processing the soil sample to generate a prepared soil sample;

analyzing the prepared soil sample with a spectrometer capable of generating spectra in a near-infrared range to generate a near-infrared spectral data set for the prepared soil sample;

inputting, with a computer, the near-infrared spectral data set into a soil texture prediction model to generate a soil texture estimate for the soil sample, the soil texture estimate comprising at least two of: a sand proportion, a silt proportion, and a clay proportion;

inputting, with a computer, the soil texture estimate into a pedotransfer function to determine a hydrological property of the soil sample; and providing the soil texture estimate.

17. The method of claim 16, wherein inputting the soil texture estimate into the pedotransfer function further comprises determining a soil organic matter content of the soil sample and inputting it into the pedotransfer function to determine the hydrological property.

18. The method of claim 16, wherein the hydrological property of the sample is one selected from the group consisting of: soil water-holding capacity, field capacity, high and low watermarks, saturation point, permanent wilting point, and plant available water.

19. The method of claim 16, wherein receiving the soil sample comprises:
identifying the soil sample and associating the soil sample with a geographic location.

20. The method of claim 16, wherein analyzing the prepared soil sample with the spectrometer comprises scanning the soil sample over a spectral range comprising 12,500 $cm^{-10}$ to 3,600 $cm^{-1}$.

* * * * *